United States Patent [19]
Alferness et al.

[11] Patent Number: 5,243,975
[45] Date of Patent: Sep. 14, 1993

[54] DEFIBRILLATOR WITH USER-INTERACTIVE SCREEN DISPLAY

[75] Inventors: Clifton A. Alferness, Redmond; Bruce E. O'Connor, Seattle, both of Wash.

[73] Assignee: Physio-Control Corporation, Redmond, Wash.

[21] Appl. No.: 738,583

[22] Filed: Jul. 31, 1991

[51] Int. Cl.$^5$ .............................................. A61N 1/39
[52] U.S. Cl. ...................................................... 607/7
[58] Field of Search ........................... 128/419 D, 734

[56] References Cited

U.S. PATENT DOCUMENTS

| | | | |
|---|---|---|---|
| 511,813 | 5/1992 | Charbonnier et al. | 128/419 D |
| 3,814,105 | 6/1974 | Howard et al. | 128/419 D |
| 4,300,575 | 11/1981 | Wilson | 128/798 |
| 4,328,808 | 5/1982 | Charbonnier | 128/419 D |
| 4,506,677 | 3/1985 | Lambert | 128/697 |
| 4,574,810 | 3/1986 | Lerman | 128/419 D |
| 4,610,254 | 9/1986 | Morgan et al. | 128/419 D |
| 4,619,265 | 10/1986 | Morgan et al. | 128/419 D |
| 4,771,781 | 9/1988 | Lerman | 128/419 D |
| 4,840,177 | 6/1989 | Charbonnier et al. | 128/419 D |

FOREIGN PATENT DOCUMENTS

| | | |
|---|---|---|
| 0246064 | 11/1987 | European Pat. Off. |
| 0437104A2 | 7/1991 | European Pat. Off. |

OTHER PUBLICATIONS

G. W. N. Dalzell, S. R. Cunningham, J. Anderson, and A. A. Jadgey, "Initial Experience With a Microprocessor Controlled Current Based Defibrillator", *Br Heart j*, 61:502-5 (1989).

*Primary Examiner*—William E. Kamm
*Assistant Examiner*—Kennedy J. Schaetzle
*Attorney, Agent, or Firm*—Christensen, O'Connor, Johnson & Kindness

[57] ABSTRACT

A defibrillator designed to determine and display (1) the current which is anticipated to be provided to a patient by a defibrillation pulse generated by the defibrillator when the former is to be provided in the form of an energy dose and (2) the energy which is anticipated to be provided to a patient by a defibrillation pulse generated by the defibrillator when the former is to be provided in the form of a current dose. The defibrillator is also designed to determine and display how changes in the transthoracic impedance of the patient will change (1) the magnitude of the selected energy level of the defibrillation pulse when the defibrillator is in the energy dose mode and (2) the magnitude of the selected current level of the defibrillation pulse when the defibrillator is in the current dose mode.

23 Claims, 4 Drawing Sheets

DEFIBRILLATOR WITH USER-INTERACTIVE SCREEN DISPLAY

FIELD OF THE INVENTION

The present invention relates generally to cardiac defibrillators, and more particularly to systems for determining and displaying characteristics of a defibrillation pulse generated by a cardiac defibrillator.

BACKGROUND OF THE INVENTION

Defibrillators have been widely used to administer a high-voltage, direct-current shock pulse to a patient undergoing cardiac arrest occurring because of asynchronous depolarization, i.e., fibrillation, of cardiac cells. When sufficient electrical energy is delivered to the heart from an external defibrillator through two or more electrodes positioned to engage the patient, fibrillation of the cardiac cells may be arrested. Thereafter, synchronous or normal depolarization of the cardiac cells will often resume.

Defibrillators are typically calibrated in terms of the energy level of the defibrillation pulse they generate, i.e., defibrillators are calibrated in terms of joules or watt seconds. Evidence also has been developed which suggests that it may be desirable to calibrate the defibrillation pulse in terms of the peak current delivered by the pulse. As a consequence, defibrillators which calibrate the defibrillation pulse they generate in this manner may become commercially available.

"Energy dose" defibrillators which display the peak current for each defibrillation pulse they provide, after the pulse is delivered, are known. For instance, in U.S. Pat. No. 4,328,808, Charbonnier et al. disclose an "energy dose" defibrillator which displays peak current, transthoracic impedance, and delivered energy for each defibrillation pulse provided by the defibrillator. Additionally, in U.S. Pat. No. 4,506,677, Lambert discloses an "energy dose" defibrillator which includes a circuit for measuring the time-dependent variation of the delivered current of a defibrillation pulse. The Lambert defibrillator inserts a representation of that variation into a recording of the patient's ECG signal after delivery of the pulse.

The Charbonnier et al. and Lambert defibrillators are not designed to display the current which is anticipated to be carried to the patient by the defibrillation pulse. Although it may be interesting to know the magnitude of the peak current carried by a defibrillation pulse after the pulse has been delivered, it is far more useful to know the magnitude of the peak current which is expected to be carried by a defibrillation pulse prior to application of the pulse. Such anticipated current, which will vary as a function of the transthoracic impedance of the patient, may be used by the health care professional operating the defibrillator in determining the placement of, and pressure to be applied to, the defibrillator paddles (electrodes) required to ensure the defibrillation pulse delivers the selected amount of energy to the patient. It is believed that no known "energy dose" defibrillators are designed to permit a user to select the current anticipated to be carried by the defibrillation pulse prior to application of the pulse or to display such selected current. "Current dose" defibrillators are disclosed in U.S. Pat. Nos. 4,574,810 and 4,771,781 to Lerman and in U.S. Pat. No. 4,840,177 to Charbonnier et al. These defibrillators automatically determine the transthoracic resistance of the patient, and use this resistance to calculate the threshold level of peak current required to effect defibrillation. The defibrillation pulse is delivered to the patient based on the calculated peak current so as to ensure the pulse does not exceed the predetermined defibrillation pulse threshold. After the defibrillation pulse is delivered, the transthoracic resistance, peak current, and delivered energy of the defibrillation pulse are displayed.

It is believed that no known "current dose" defibrillators display the energy which is anticipated to be discharged by the defibrillation pulse prior to application of the pulse. Information regarding the anticipated energy to be provided by the defibrillation pulse may be used by the health care professionals administering the pulse, particularly those professionals who tend to think of defibrillation pulses in terms of the energy delivered by the pulse, in optimizing the placement and pressure of the defibrillation paddles.

SUMMARY OF THE INVENTION

The present invention is a defibrillator which is designed to permit a user to select whether the defibrillation pulse is to be provided as a "current dose" or as an "energy dose." The defibrillator is also designed to continuously determine and display the anticipated current equivalent of a selected "energy dose" and the anticipated energy equivalent of a selected "current dose" as a function of the transthoracic impedance of the patient. In this connection, the defibrillator is designed to continuously measure the transthoracic impedance of the patient. As an optional feature, the defibrillator may be designed to continuously calculate and display changes in the magnitude of the selected energy level or current level, as the case may be, based on changes in the transthoracic impedance of the patient.

The present invention also encompasses a system designed for use with a "current dose", an "energy dose", or a combined "current/energy dose" defibrillator, for continuously calculating and displaying, prior to application of the defibrillation pulse, the anticipated energy equivalent of a selected "current dose" or the anticipated current equivalent of a selected "energy dose." Because the anticipated "energy dose" or "current dose" will vary as a function of the transthoracic impedance of the patient, the present system is adapted for use with a defibrillator of the type including means for continuously measuring the transthoracic impedance of the patient prior to application of the defibrillation pulse. In this connection, the present system is designed to continuously calculate the anticipated current dose or energy dose based on the transthoracic impedance measured by the impedance measuring means of the defibrillator.

BRIEF DESCRIPTION OF THE DRAWINGS

In the FIGURES, like reference numerals refer to like components.

DETAILED DESCRIPTION OF THE INVENTION

Figure 1:
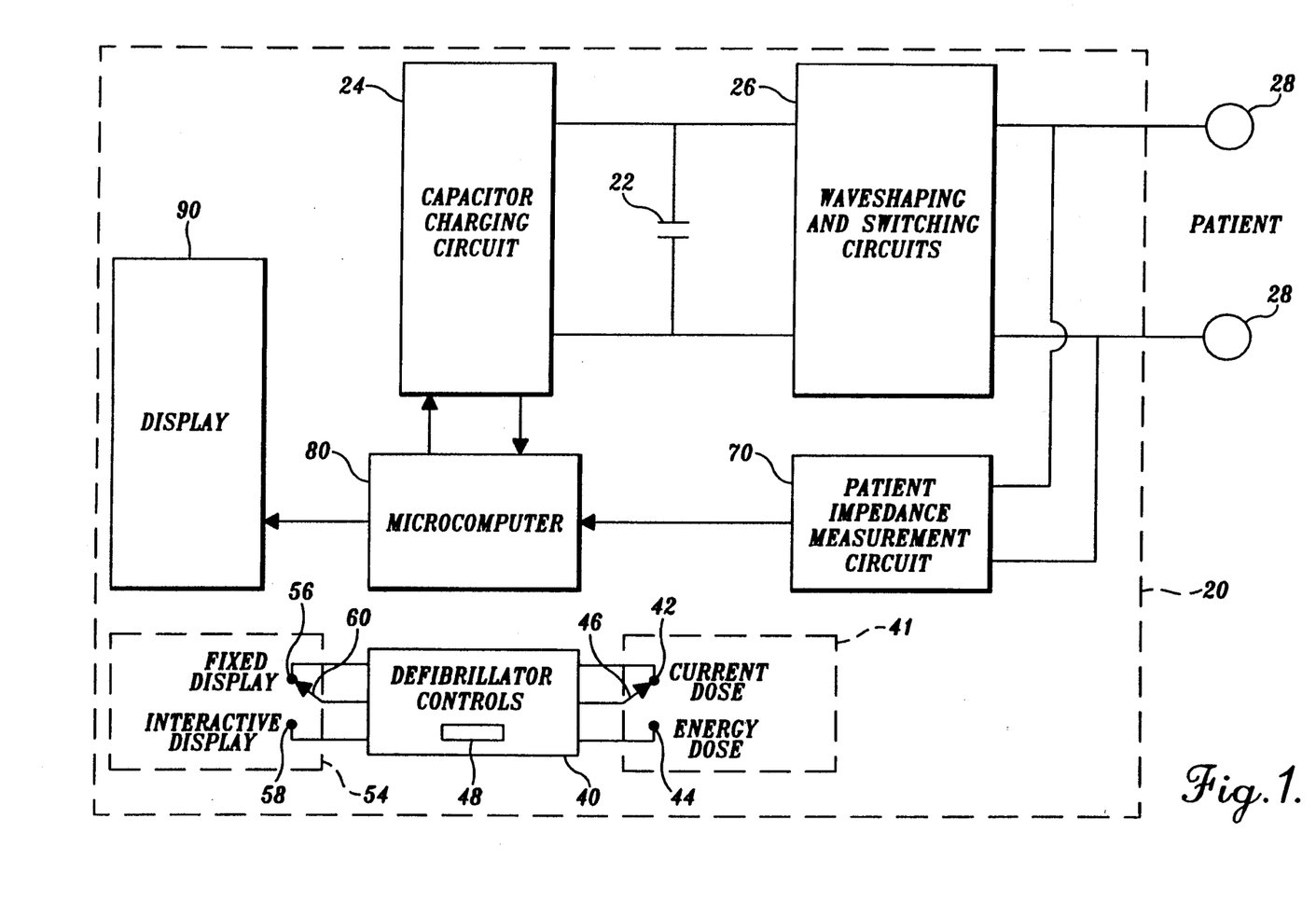
FIG. 1 is a schematic block diagram of the defibrillator of the present invention.

Referring to FIG. 1, the present invention is a defibrillator which is operable in either a "current dose" or an "energy dose" mode. The defibrillator is designed to determine and display the current which is anticipated to be delivered by the defibrillation pulse when the defibrillator is in the "energy dose" mode and the anticipated energy to be discharged by the defibrillation pulse when the defibrillator is in the "current dose" mode. As used herein, "energy dose" refers to a defibrillation pulse which is calibrated and provided in terms of the energy to be discharged by the pulse, and "current dose" refers to a defibrillation pulse which is calibrated and provided in terms of the peak current to be delivered by the defibrillation pulse.

Defibrillator 20 is similar to defibrillators of the type disclosed in U.S. Pat. No. 4,619,265 to Morgan et al., which patent is incorporated herein by reference, except that, as discussed hereinafter, defibrillator 20 includes a patient impedance measurement circuit 70, and the microcomputer 80 of the defibrillator is programmed in a unique manner.

Defibrillator 20 includes a conventional capacitor 22 for storing a selected charge. In the preferred embodiment of the present invention, capacitor 22 is designed to store a charge having a voltage of up to about 5,000 volts. Capacitor 22 is coupled between capacitor charging circuit 24 and waveshaping and switching circuits 26.

Capacitor charging circuit 24 causes capacitor 22 to charge to a level selected by the user of defibrillator 20, as discussed in greater detail hereinafter, and ensures that capacitor 22 remains charged at the selected level. Capacitor charging circuit 24 is a conventional circuit of the type used in the defibrillator disclosed in U.S. Pat. No. 4,619,265, or U.S. Pat. No. 3,814,105, the latter patent also being incorporated herein by reference.

Waveshaping and switching circuits 26 shape the charge released by capacitor 22 so that the shock pulse delivered by defibrillator 20 possesses the desired characteristics. Additionally, circuits 26 provide a switching function. More specifically, circuits 26 typically comprise a high voltage relay which delivers energy stored in capacitor 22 through a waveshaping inductor (not shown) to the electrode paddles. Waveshaping and switching circuits 26 may comprise a waveshaping and switching circuit of the type employed in U.S. Pat. No. 4,619,265.

Defibrillator 20 includes a pair of electrode paddles 28 which are attached to circuits 26 so as to receive the shaped energy pulse delivered through circuits 26. Electrode paddles 28 may be hand-held electrodes of the type used with the defibrillator disclosed in U.S. Pat. No. 4,619,265 or self-adhesive electrodes of the type disclosed in U.S. Pat. No. 4,300,575.

Defibrillator 20 also comprises defibrillator controls 40. The latter comprises switch 41 which includes terminals 42 and 44, and relay 46. The latter is designed to be electrically couplable with either terminal 42 or terminal 44. Defibrillator 20 operates in a current dose mode when relay 46 engages terminal 42, and defibrillator 20 operates in an energy dose mode when relay 46 engages terminal 44.

Defibrillator controls 40 additionally comprise a switch 48 for selecting the desired quantity of current to be delivered by the defibrillation pulse when relay 46 engages terminal 42 (i.e., when defibrillator 20 is in the current dose mode), and for controlling, the quantity of energy to be discharged by the defibrillation pulse when relay 46 engages terminal 44 (i.e., when defibrillator 20 is in the energy dose mode).

As an optional feature, defibrillator controls 40 may include switch 54 for setting defibrillator 20 in either a fixed display mode or in an interactive display mode, as discussed hereinafter. Switch 54 comprises terminals 56 and 58, and relay 60 which is designed to be electrically couplable with either terminal 56 or terminal 58. As discussed in greater detail hereinafter, when relay 60 engages terminal 56, defibrillator 20 will operate in the fixed display mode, and when relay 60 engages terminal 58 defibrillator 20 will operate in the interactive display mode.

Defibrillator 20 comprises a patient impedance measurement circuit 70 for continuously measuring the transthoracic impedance of the patient requiring defibrillation. Measurement circuit 70 is coupled between waveshaping and switching circuits 26 and paddles 28. Measurement circuit 70 is designed to repeatedly sample the patient's transthoracic impedance to a small alternating current excitation signal. U.S. Pat. No. 4,840,177 to Charbonnier et al. discloses a patient impedance measurement circuit which may be satisfactorily employed as circuit 70, which patent is incorporated herein by reference.

Defibrillator 20 further comprises a conventional microcomputer 80 which is coupled to capacitor charging circuit 24, defibrillator controls 40, patient impedance measurement circuit 70, and energy display 90, the latter being described hereinafter. Microcomputer 80 includes a microprocessor (not shown), read-only memory (ROM) (not shown), and read-write memory (RAM) (not shown). Microcomputer 80 is programmed in a known manner to control the operation of capacitor charging circuit 24 based on information contained in the input signal provided from defibrillator controls 40. Except as described hereinafter, microcomputer 80 controls the operation of display 90 in a conventional manner.

Figure 2:
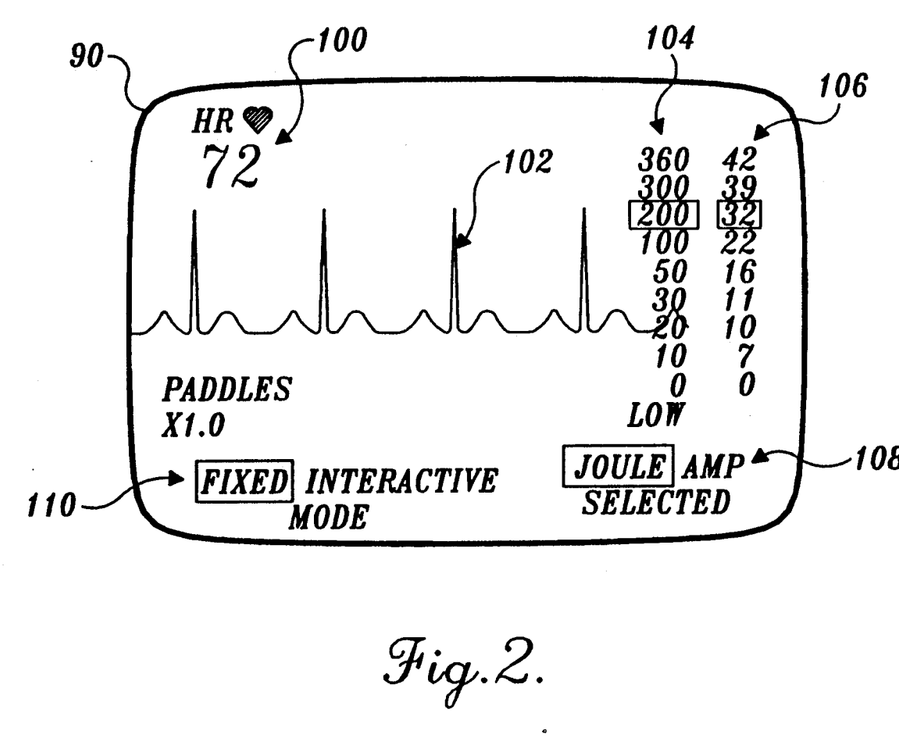
FIG. 2 is an exemplary screen display of the defibrillator of the present invention.

Referring to FIGS. 1 and 2, display 90 is a conventional visual display, such as a liquid crystal display or cathode ray tube display, of the type widely used on known defibrillators to display information regarding (1) the heart beat of the patient undergoing defibrillation and (2) the energy and current of the transmitted defibrillation pulse and the transthoracic impedance of the patient.

As indicated in FIG. 2, microcomputer 80 controls the operation of display 90 based on information received from electrodes (not shown) attached to the patient so that the screen of display 90 indicates the heart rate of the patient in numerical form, as indicated at 100, and provides a wavetrain 102 indicating the morphology of the patient's heartbeat. Microcomputer 80 also causes a column 104 of predetermined energy level values to be displayed on the screen of display 90. For instance, as illustrated in FIG. 2, in a preferred embodiment of the invention microcomputer 80 causes a column 104 having nine discrete predetermined energy levels ranging from 0 to 360 joules to be displayed on the screen of display 90. As described thus far, the manner in which microcomputer 80 generates the display on the screen of display 90 is well known in the art.

Referring to FIGS. 1-4, microcomputer 80 is also programmed to provide additional, unique information on the screen of display 90. This additional information includes a column 106 of discrete current levels, each of which is positioned adjacent a discrete, associated energy level. For a given energy level, the associated current level will be the peak current which is anticipated to be delivered by the defibrillation pulse when provided at the given energy level. As described below in greater detail in connection with the software flow diagrams illustrated in FIGS. 3 and 4, the current level values initially provided in column 106 are predetermined. However, these current level values may change based on changes in the transthoracic impedance of the patient measured by impedance measurement circuit 70. Microcomputer 80 causes other unique information to be illustrated on the screen of display 90, including an identification of whether defibrillator 20 is in the current dose mode or the energy dose mode, as indicated at 108 in FIG. 2. Additionally, if microcomputer 80 is programmed to permit the current and energy level information provided in columns 104 and 106 to be displayed in either a fixed or a user-inactive mode, as discussed hereinafter, an indication will be provided on the screen of display 90, as indicated at 110, regarding the mode in which the defibrillator has been directed to operate.

Figure 3:
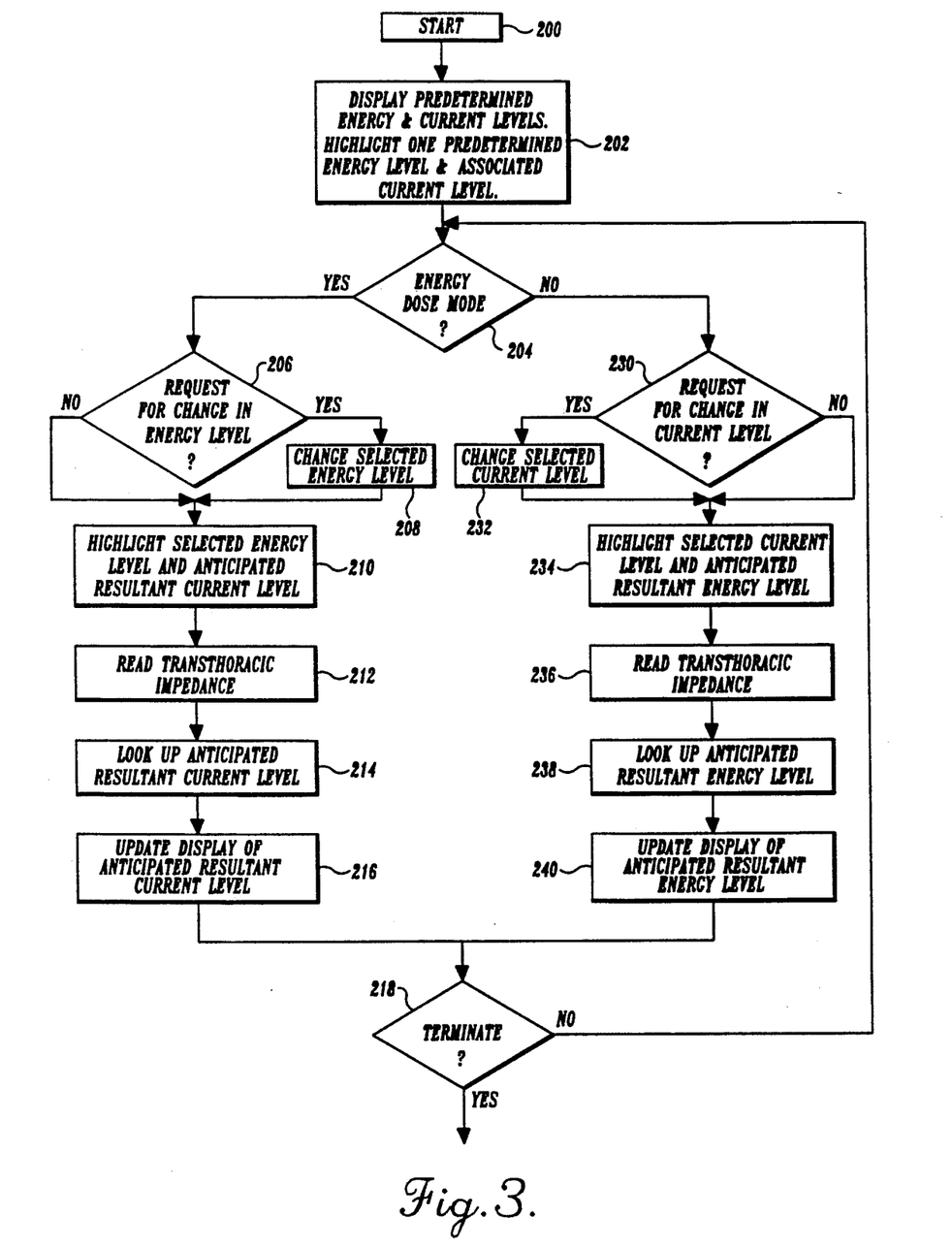
FIG. 3 is a flow diagram of one embodiment of the software used by the microcomputer of the defibrillator for determining and updating anticipated current and/or energy equivalents.

When microcomputer 80 is programmed to display current and energy levels in a fixed mode format, the microcomputer generates the energy and current level information contained in columns 104 and 106, and the energy/current dose format information provided in row 108, in accordance with a software program represented by the flow diagram illustrated in FIG. 3. The code for this software is not listed herein inasmuch as (1) one of ordinary skill in the art could readily generate such code based on the flow diagram illustrated in FIG. 3, and (2) the code will vary to some extent depending upon the computer on which it is implemented.

After the software program has been started, as indicated at step 200, the program causes predetermined energy and current values to be displayed in columns 104 and 106, respectively, and highlights one predetermined energy level and an associated current level, as indicated at step 202. In the exemplary embodiment illustrated in FIG. 2, microcomputer 80 causes nine predetermined energy levels ranging from 0 to 360 joules, and nine corresponding current levels ranging from 0 to 42 amperes to be displayed on the screen of display 90. As part of step 202, the units of displayed energy and current are indicated below columns 104 and 106, i.e., the word "joule" is displayed below column 104 and the word "amp" is displayed below column 106.

Next, at step 204, a determination is made as to whether switch 41 is in the energy dose mode, as occurs when relay 46 is in contact with terminal 44. If at step 204 it is determined that defibrillator 20 has been switched to the energy dose mode, then the routine proceeds to step 206. There, a determination is made if a request for change in the energy level of the defibrillation pulse has been made. Such a request is made by adjusting switch 48 of defibrillator controls 40. If the desired energy level has been changed, then the routine proceeds to step 208 where the energy level indicated on the screen of display 90 is changed from the last selected energy level to the currently selected energy level. Thereafter the routine proceeds to step 210. If no request for change in energy level has been made at step 206, then the routine proceeds directly to step 210.

At step 210, microcomputer 80 causes display 90 to highlight the selected energy level and the anticipated results current level associated with the selected energy level. This highlighting is accomplished by encircling the selected energy level and anticipated resultant current level, by displaying the selected energy level and anticipated resultant current level in reverse video mode, or by using other known means for highlighting. The anticipated resultant current level displayed at step 210 is the peak current which is anticipated to be delivered by the defibrillation pulse when provided at the selected energy level. Additionally at step 210, the word "JOULE" positioned below column 104 is highlighted.

Next, at step 212, microcomputer 80 reads and temporarily stores the transthoracic impedance output provided by impedance measurement circuit 70.

During the first iteration of the loop beginning with step 206 and terminating with step 218, the anticipated resultant current will be the associated current level highlighted at step 202. During subsequent iterations of this loop, as indicated at step 214, microcomputer 80 will look up the anticipated resultant current level associated with the selected energy level in a look-up table stored in its static memory. The look-up table in microcomputer 80 is structured such that it comprises a plurality of anticipated resultant current levels. Each of the latter is identified by a unique two-part address. The first part of the address is the selected energy level highlighted at step 210 and the second part of the identifier is the transthoracic impedance measured at step 212 during the current iteration of the loop which begins with step 206 and ends with step 218. Thus, for example, if the selected energy level is 200 joules and the transthoracic impedance last measured at step 212 is 50 ohms, microcomputer 80 will review the address list of its look-up table until it finds an address having these values. After this address is located, the microcomputer will read the current level associated with the address. In one version of the look-up table, the anticipated resultant current level associated with a selected energy level of 200 joules and a transthoracic impedance of 50 ohms is 32 amperes. Typically, the look-up table for microcomputer 80 is programmed based on empirically derived data.

Then, at step 216, microcomputer 80 updates the anticipated resultant current level associated with the selected energy level and displayed on the screen of display 90 so as to correspond with the current level found in the look-up table of the microcomputer at step 214.

The routine then proceeds to step 218 where a determination is made if a terminate command has been received. If so, the routine terminates. If a terminate command has not been received, then the routine loops back to step 204 where determination is again made if defibrillator controls 40 have been set so as to cause defibrillator 20 to operate in the energy dose mode.

If at step 204 it is determined that defibrillator controls 40 have been set in the current dose mode, i.e., relay 46 has been moved into contact with terminal 42, then the routine illustrated in FIG. 3 proceeds to step 230.

At step 230, a determination is made if a request has been entered for a change in the selected current level. Such request is effected by appropriate adjustment of switch 48 of defibrillator controls 40. When the routine arrives at step 230, the selected current level will be either (1) the current level highlighted at step 202 if the routine has proceeded from step 202 through step 204 to step 230 without any other intervening steps, (2) the anticipated resultant current level associated with the energy level last selected during the last iteration of the loop comprising steps 206–216, if the determination made at step 204 during the immediately preceding iteration of the routine was made in the affirmative, or (3) the current level last selected at step 232. In this connection, if it is determined that a request for change in current level has been made at step 230, then the routine proceeds to step 232 where the selected current level is changed based on instructions provided by the user of defibrillator 20 via switch 48 of defibrillator controls 40. After step 232, the routine proceeds to step 234. If, at step 230, it is determined that no request has been made for change in selected current level, then the routine proceeds to step 234.

At step 234, microcomputer 80 highlights the selected current level and anticipated resultant energy level illustrated on the screen of display 90. When defibrillator 20 is in the current dose mode, the anticipated resultant energy level will be the energy which is anticipated to be discharged by the defibrillation pulse when delivered at the selected current level. Also at step 234, the word "amp" positioned below column 106 is highlighted.

Then, the routine proceeds to step 236 where microcomputer 80 reads and temporarily stores the transthoracic impedance currently provided in the output signal of impedance measurement circuit 70.

Thereafter, the routine proceeds to step 238 where microcomputer 80 looks up the anticipated resultant energy level associated with the selected current level in a second look-up table. The latter includes a plurality of anticipated resultant energy levels, each of which is identified by a two-part address. The first part of the address is the selected current level highlighted at step 234 and the second part of the address is the transthoracic impedance read at step 236. In an exemplary second look-up table stored in microcomputer 80, the anticipated resultant energy level identified by an address comprising a current level of 40 amperes and an impedance level of 45 ohms is 320 joules. The second look-up table is also programmed based on empirically derived data.

The routine proceeds from step 238 to step 240 where microcomputer 80 updates the anticipated resultant energy level displayed on the screen of display 90 so that it corresponds to the anticipated resultant energy level located in the second look-up table at step 238.

Finally, the routine proceeds to step 218 where determination is made if a terminate command has been received, as discussed above.

The software program represented by the flow diagram illustrated in FIG. 3 is designed so that any change in the position or pressure of paddles 28 on the patient will cause the anticipated resultant energy level or anticipated resultant current level, depending upon whether defibrillator 20 is in the current or energy dose mode, respectively, indicated on the screen of display 90 to change. By constant monitoring of these changes in the anticipated resultant energy or current levels, the health care professional using defibrillator 20 is able to select the placement and pressure of paddles 28 necessary to ensure the defibrillation pulse to be applied to the patient has the desired current and energy characteristics. By optimizing the energy to be discharged by, and the current to be delivered by, the defibrillation pulse, the possibility of either injuring the patient or not achieving successful defibrillation may be reduced significantly.

With the program in microcomputer 80 represented by the software flow diagram illustrated in FIG. 3, the selected current level or selected energy level, as the case may be, does not change with changes in the position or pressure of electrodes 28 on the patient. Under certain circumstances, however, it may be desirable to additionally indicate how changes in the placement of electrodes 28 or changes in the transthoracic impedance of the patient affect the selected energy level or selected current level. To this end, microcomputer 80 may alternatively be programmed in accordance with the software flow diagram illustrated in FIG. 4. Again, line by line coding of such programming is not provided inasmuch as it is believed that one of ordinary skill in the art could readily perform such programming based on the flow diagram illustrated in FIG. 4.

Figure 4:
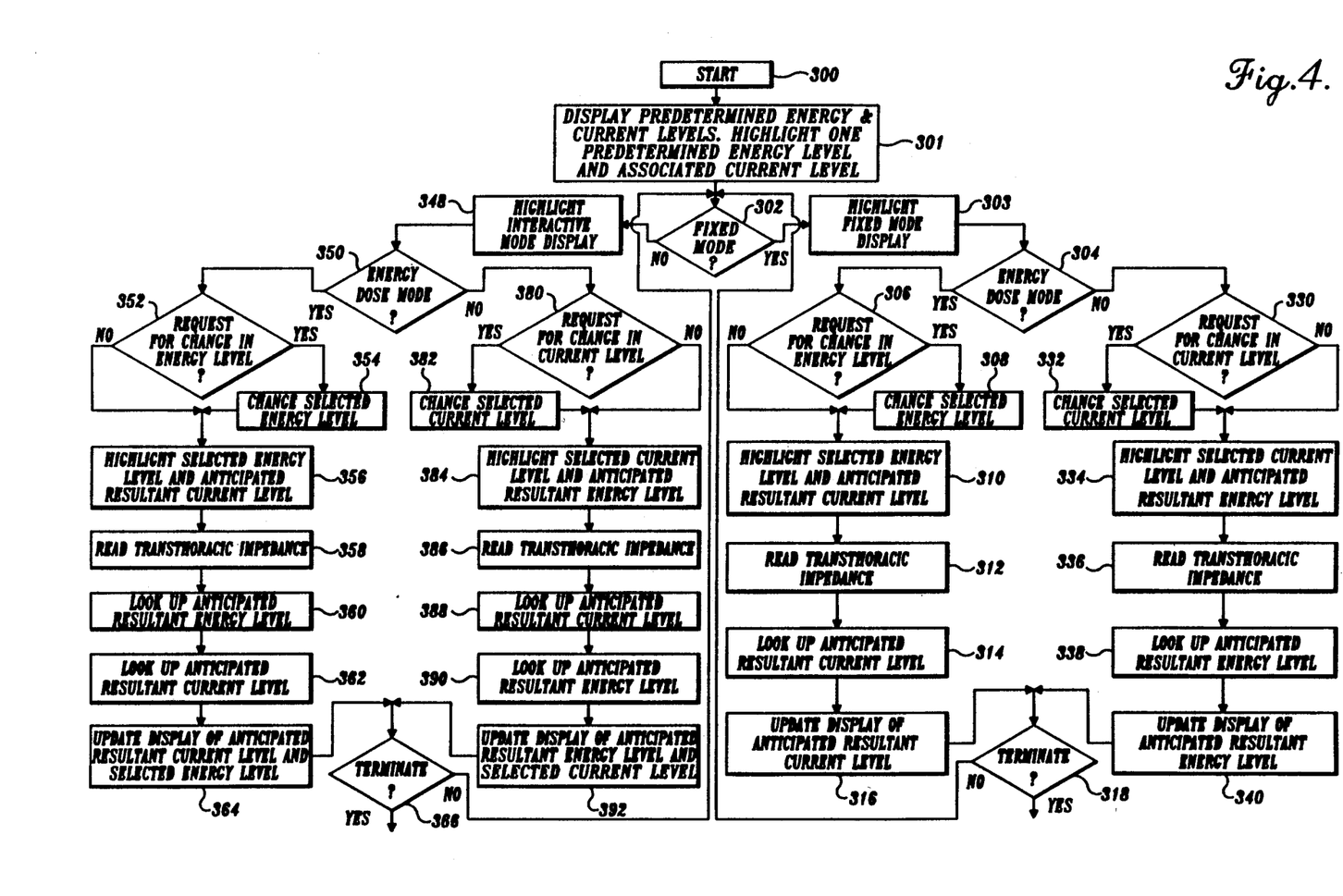
FIG. 4 is a flow diagram of another embodiment of the software program used by the microcomputer of the defibrillator for determining and updating both anticipated and selected energy and current levels indicated on the screen display of the defibrillator.

The first two steps of the flow diagram illustrated in FIG. 4, steps 300 and 301, are identical to the first two steps in the flow diagram illustrated in FIG. 3. The routine proceeds from step 301 to step 302 where a determination is made if switch 54 of defibrillator controls 40 has been switched to the fixed mode. In the fixed mode, relay 60 of switch 40 will engage terminal 56, as illustrated in FIG. 1, and the selected energy level or selected current level, as the case may be, indicated on display 90 will not change with changes in transthoracic impedance.

In the event the determination made at step 302 reveals that switch 54 has been set in the fixed mode, the routine proceeds to step 303. There, microcomputer 80 causes the word "fixed" appearing at 110 on the screen of display 90 to be highlighted.

Next, the routine proceeds to step 304. The branch of the routine illustrated in FIG. 4 beginning with step 304 and terminating with step 318, including steps 306–316 and steps 330–340, is identical to the portion of the software flow diagram illustrated in FIG. 3 beginning at step 204 and ending at step 218, including steps 206–216 and 230–240. Thus, for instance, step 204 is identical to step 304, and step 238 is identical to step 338. For a description of the functions performed by steps 304–318 and 330–340, attention is directed to the description of steps 204–218 and 230–240 set forth above.

If the determination made at step 303 reveals that switch 54 has been set to the interactive mode, i.e., relay 68 has been moved into contact with terminal 58, the routine will proceed from step 303 to step 348 where the word "interactive" is highlighted on the screen of display 90. As described below in greater detail, when defibrillator 20 is operated in the interactive mode, both the anticipated resultant current level or anticipated resultant energy level, as the case may be, as well as the selected energy level or selected current level, also as the case may be, will change with changes in the transthoracic impedance measured by impedance measurement circuit 70.

The branch of the software flow diagram illustrated on the left side of FIG. 4, i.e., the branch beginning with step 350 and terminating with step 366, including steps 352–364 and 380–392, is identical to the right hand branch of the flow diagram illustrated in FIG. 4, i.e., the branch beginning with step 304 and ending with step 318, including steps 306–316 and steps 330–340, except that the display of both the current levels and the energy levels is updated at step 364 and 392 in the left hand branch, and the left hand branch includes steps 360 and 388. Thus, for all but steps 364 and 392, and steps 360 and 388, a description of the operations performed in the left hand branch of the flow diagram illustrated in FIG. 4 may be obtained by referring to the foregoing description of the right hand branch of this flow diagram, which description is predicated on the preceding description of the flow diagram illustrated in FIG. 3.

As to step 360, after an affirmative determination has been made at step 350 and the routine has proceeded down the branch comprising steps 352, 356, and 358 to step 360, microcomputer 80 will look up the anticipated resultant energy level associated with the selected energy level which was highlighted at step 356, as discussed in the following paragraph. The anticipated resultant energy level is the quantity of energy which is anticipated to actually be discharged by the defibrillation pulse when provided at the selected energy level. Any disparity between the selected energy level and the anticipated resultant energy level typically occurs as a result of changes in the transthoracic impedance of the patient. Step 360 is added to provide the health care professional using defibrillator 20 with information regarding how changes in position or pressure of electrodes 28 will affect the previously selected energy level of the defibrillation pulse.

At step 360, microcomputer 80 reviews a third look-up table in its memory comprising a plurality of anticipated resultant energy levels, each of which is identified by a unique two-part address comprising a current level and an impedance level. This review continues until microcomputer 80 locates an address comprising the current level last highlighted at step 356 and the impedance value last read at step 358. As indicated at step 364, the energy level associated with this address is then displayed in place of the selected energy level last highlighted at step 356. As at step 316, the anticipated resultant current level is also updated at step 364.

Microcomputer 80 performs a similar function at step 388, except that it uses a fourth look-up table comprising a plurality of current levels, each of which is identified by a two-part address comprising an energy level and an impedance level. When the microcomputer locates an address comprising the energy level last highlighted at step 384 and the impedance value last read at step 386, the anticipated resultant current level located at step 388 is then displayed in place of the selected current level last highlighted at step 384, as indicated at step 392. Also at step 392, the anticipated resultant energy level indicated by display 90 is updated.

As described above, the present invention is a defibrillator capable of generating a defibrillation pulse as either a current dose or an energy dose. It is to be appreciated, however, that the present invention also encompasses an energy dose defibrillator designed to provide anticipated resultant current level information for a selected energy level, and which optionally may be designed to operate in either a fixed or an interactive mode. The anticipated resultant current level is determined by such an energy dose defibrillator in the manner described above in connection with energy/current dose defibrillator 20 when the latter is operated in the energy dose made. Similarly, the present invention encompasses a current dose defibrillator which is designed to provide anticipated resultant energy level information with respect to the selected current level, and which optionally may be designed to operate in either a fixed or an interactive mode. Such a current dose defibrillator is designed to determine and display anticipated resultant energy level information in the same manner that defibrillator 20 calculates anticipated resultant energy levels when operated in the current dose mode, as described above.

Moreover, the present invention encompasses a system designed for use with either an energy dose defibrillator, a current dose defibrillator, or an energy/current dose defibrillator, which three types of defibrillators include impedance-measuring means for continuously measuring the transthoracic impedance of the patient, for determining and displaying anticipated resultant current and energy level information with respect to the associated selected current and energy levels of the defibrillation pulse, as the case may be. Assuming the defibrillator with which such a system is coupled comprises capacitor charging and wave-shaping circuits, such as circuits 24 and 26, defibrillation controls, such as controls 40, and an impedance measurement circuit, such as circuit 70, a microcomputer, such as microcomputer 80, and a display such as display 90, such an add-on system may comprise merely an additional microcomputer module (not shown) which is coupled with the microcomputer of the defibrillator. This coupling must be effected so that the microcomputer module is coupled with the capacitor charging circuit, the impedance measurement circuit, the defibrillator controls and the display. The add-on microcomputer module is programmed in accordance with the software flow diagram illustrated in either FIG. 3 or 4, as desired. Such an add-on system may alternatively be coupled with the existing defibrillator merely by programming the microcomputer of the former in accordance with the software flow diagram illustrated in FIG. 3 or 4, as preferred.

Although optimal results are achieved when defibrillator 20 comprises impedance measurement circuit 70, in an alternative embodiment of the defibrillator, impedance measurement circuit 70 is eliminated and the look-up tables in microcomputer 80 include a fixed impedance value, e.g., 50 ohms, in the address portion of the look-up tables. With such an alternative embodiment, the anticipated resultant energy or current level will not change with changes in the position or pressure of electrodes 28 on the patient.

An important advantage of the present invention is that defibrillator 20 will provide anticipated resultant current or energy level information, depending upon whether the defibrillator is in the energy dose or current dose mode, respectively, before the defibrillation pulse is applied to the patient. Such anticipated resultant current or energy level information may be used by the health care professional administering the defibrillation pulse so as to ensure the pulse is sufficient to effect defibrillation while simultaneously minimizing the risk of additional injury to the patient. With known defibrillators, the current level associated with an energy dose pulse or the energy level associated with a current dose pulse is determined and displayed only after the defibrillation pulse has been applied. Although such "after the fact" information may be useful in optimizing delivery of subsequent defibrillation pulses, the first-applied defibrillation pulses are frequently too weak or too strong with such known defibrillators.

Another important advantage of the present invention is that it assists a health care professional accustomed to thinking of a defibrillation pulse in terms of the energy discharged by the pulse to also consider the defibrillation pulse in terms of the current delivered by the pulse. Such "education" of the health care professional occurs because the current level associated with the selected energy level is displayed and constantly updated as the defibrillator is used.

Since certain changes may be made in the above apparatus without departing from the scope of the invention herein involved, it is intended that all matter contained in the above description or shown in the accompanying drawings shall be interpreted in an illustrative and not in a limiting sense.

The embodiments of the invention in which an exclusive property or privilege is claimed are defined as follows:

1. A defibrillator comprising:
   generator means for generating a defibrillation pulse;
   electrode means for delivering the defibrillation pulse to a patient;
   control means coupled to said generator means for permitting a user of the defibrillator to select (1) if the defibrillation pulse generated by said generator means is to be delivered to the patient as an energy dose or as a current dose, and (2) the magnitude of the energy dose or the current dose; and
   determination means coupled to said control means (1) for determining prior to delivery of a defibrillation pulse to be delivered as a selected current dose, an energy equivalent which is the energy anticipated to be delivered by the defibrillation pulse, and (2) for determining prior to delivery of a defibrillation pulse to be delivered as a selected energy dose, a current equivalent which is the current anticipated to be delivered by the defibrillation pulse.

2. A defibrillator according to claim 1, further comprising display means coupled to said control means and said determination means for visually displaying said energy equivalent and said current equivalent determined by said determination means.

3. A defibrillator according to claim 2, further wherein said display means is designed to display:
   (a) whether the defibrillation pulse is to be delivered in the form of a current dose or an energy dose; and
   (b) the selected current level of the defibrillation pulse when the defibrillation pulse is to be delivered as a current dose and the selected energy level of the defibrillation pulse when the defibrillation pulse is to be delivered as an energy dose.

4. A defibrillator according to claim 1, further comprising impedance measuring means for continuously measuring the transthoracic impedance between said patient and said generator means.

5. A defibrillator according to claim 4, wherein said determination means is coupled with said impedance measuring means, and said determination means is designed to continuously determine said current equivalent and said energy equivalent as a function of the impedance measured by said impedance measuring means.

6. A defibrillator according to claim 1, wherein said determination means is additionally designed to determine (1) prior to delivery of a defibrillation pulse to be delivered as a selected current dose, the current which is anticipated to be delivered by the defibrillation pulse, and (2) prior to delivery of a defibrillation pulse to be delivered as a selected energy dose, the energy which is anticipated to be delivered by the defibrillation pulse.

7. A defibrillator according to claim 6, further wherein:
   said control means includes selection means for permitting a user of the defibrillator to instruct said determination means to determine said current which is anticipated to be delivered when said defibrillation pulse is to be delivered as a selected current dose and said energy which is anticipated to be delivered when said defibrillation pulse is to be delivered as a selected energy dose; and
   said determination means is designed to determine said current which is anticipated to be delivered when said defibrillation pulse is to be delivered as a selected current dose and said energy which is anticipated to be delivered when said defibrillation pulse is to be delivered as a selected energy dose, but only when so instructed by said control means.

8. A defibrillator according to claim 7, further comprising display means coupled to said control means and said determination means for visually displaying:
   (a) if the defibrillation pulse is to be delivered in the form of a current dose or an energy dose;
   (b) the selected current level of the defibrillation pulse when the defibrillation pulse is to be delivered as a current dose and the selected energy level of the defibrillation pulse when the defibrillation pulse is to be delivered as an energy dose;
   (c) said energy equivalent and said current equivalent determined by said determination means; and
   (d) if said determination means has been instructed by said selection means to determine the energy which is anticipated to be delivered when the defibrillation pulse is to be delivered as an energy dose and the current which is anticipated to be delivered when the defibrillation pulse is to be delivered as a current dose.

9. A defibrillator according to claim 1, wherein said determination means comprises:
   a first look-up table comprising a plurality of energy level values, each being identified by a unique address comprising an associated current level value; and
   a second look-up table comprising a plurality of current level values, each being identified by a unique address comprising an associated energy level value.

10. A defibrillator comprising:
    generator means for generating a defibrillation pulse;
    electrode means for delivering the defibrillation pulse from the generator means to a patient;
    control means for permitting a user of the defibrillator (1) to select if the defibrillation pulse is to be delivered as an energy dose or as a current dose, and (2) to choose the magnitude of the selected energy dose or current dose; and
    determination means coupled with said electrode means and said control means (a) for determining the quantity of current which is anticipated to be delivered to the patient by the defibrillation pulse when the defibrillation pulse is to be delivered as an energy dose and (2) for determining the quantity of energy which is anticipated to be delivered to the patient by the defibrillation pulse when the defibrillation pulse is to be delivered as a current dose.

11. A defibrillator according to claim 10, further comprising display means coupled with said determination means for displaying:
   (a) if the defibrillation pulse is to be delivered as an energy dose or as a current dose; and
   (b) the magnitude of said current which is anticipated to be delivered and said energy which is anticipated to be delivered.

12. An energy dose defibrillator comprising:
   generator means for generating a defibrillation pulse in the form of an energy dose;
   control means coupled to said generator means for permitting a user of the defibrillator to select the energy level of the defibrillation pulse to be generated by said generator means; and
   determination means coupled to said control means for determining, prior to generation of a defibrillation pulse, a current equivalent which is the current anticipated to be delivered by the defibrillation pulse.

13. A defibrillator according to claim 12, further comprising display means coupled to said control means and said determination means for visually displaying said current equivalent determined by said determination means.

14. A defibrillator according to claim 13, further wherein said display means is designed to visually display the energy level of the defibrillation pulse selected by the user of the defibrillator.

15. A defibrillator according to claim 12, further comprising impedance measuring means for continuously measuring the transthoracic impedance between a patient and said generator means.

16. A defibrillator according to claim 12, wherein said determination means is additionally designed to determine, prior to application of the defibrillation pulse to be provided as an energy dose, the energy which is anticipated to be discharged by the defibrillation pulse.

17. A defibrillator according to claim 15, wherein said determination means is coupled with said impedance measuring means, and said determination means is designed to continuously determine said current equivalent and said energy equivalent as a function of the impedance measured by said impedance measuring means.

18. A defibrillator comprising:
   generator means for generating a defibrillation pulse in the form of an energy dose or a current dose;
   electrode means for delivering the defibrillation pulse to a patient;
   control means coupled to said electrode means for permitting a user of the defibrillator to select the energy level of the energy dose when the defibrillation pulse is delivered as an energy dose or the current level of the current dose when the defibrillation pulse is delivered as a current dose; and
   determination means coupled to said control means for determining, prior to generation of a defibrillation pulse, a current equivalent, which is the current anticipated to be delivered to the patient if the defibrillation pulse is delivered as an energy dose or an energy equivalent, which is the energy anticipated to be discharged by the defibrillation pulse if the defibrillation pulse is delivered as a current dose.

19. A system, for use with a defibrillator of the type capable of delivering a defibrillation pulse to a patient in the form of a current dose or an energy dose, for calculating and displaying the energy which is anticipated to be delivered by a defibrillation pulse delivered as a selected current dose and the current which is anticipated to be delivered by a defibrillation pulse delivered as a selected energy dose, the defibrillator further being of the type including control means for permitting a user to select the quantity of energy or current to be delivered by the defibrillation pulse, and generator means for generating said defibrillation pulse and electrode means for delivering said defibrillation pulse to the patient, the system comprising:
   first means, couplable with the defibrillator, for determining an energy equivalent, which is the energy anticipated to be delivered by a defibrillation pulse to be delivered at a current level selected with the control means of the defibrillator, and for determining a current equivalent, which is the current anticipated to be delivered by a defibrillation pulse to be delivered at an energy level selected with the control means of the defibrillator; and
   second means, coupled with said first means, for visually displaying (1) the quantity of current selected using the control means of the defibrillator and said energy equivalent of the selected current determined by said first means, and (2) the quantity of energy selected using the control means of the defibrillator and said current equivalent of the selected energy determined by said first means.

20. A system according to claim 19, wherein said first means is designed to determine said energy equivalent and said current equivalent as a function of a predetermined impedance between the generator means of the defibrillator and the patient.

21. A system according to claim 19, wherein the defibrillator with which the system is used comprises impedance detecting means for determining the transthoracic impedance between the generator means and the patient;
   further wherein said first means is couplable with the impedance detecting means of the defibrillator and is designed to determine said energy equivalent and said current equivalent as a function of the transthoracic impedance determined by the impedance detecting means.

22. A system according to claim 21, wherein the impedance detecting means of the defibrillator is designed to determine the impedance between the patient and the generator means on a substantially continuous basis;
   further wherein said first means is designed to determine said energy equivalent and said current equivalent on a substantially continuous basis.

23. A system, for use with a defibrillator of the type capable of providing a defibrillation pulse to a patient in the form of an energy dose, for calculating and displaying the current which is anticipated to be delivered by a defibrillation pulse provided as a selected energy dose, the defibrillator further being of the type including control means for permitting a user to select the quantity of energy to be provided by the defibrillation pulse, and generator means for generating said defibrillation pulse and electrode means for delivering said defibrillation pulse to the patient, the system comprising:
   first means, couplable with the defibrillator, for determining a current equivalent which is the current anticipated to be delivered by a defibrillation pulse to be delivered at an energy level selected with the control means of the defibrillator; and second means, coupled with said first means, for visually displaying (a) the energy dose level selected using the control means of the defibrillator and (b) said current equivalent of the selected energy dose level determined by said first means.

* * * * *